(12) United States Patent
Tidow et al.

(10) Patent No.: US 9,688,619 B2
(45) Date of Patent: Jun. 27, 2017

(54) PROCESS FOR OBTAINING ORGANIC ISOCYANATES FROM DISTILLATION RESIDUES FROM ISOCYANATE PREPARATION

(71) Applicant: Covestro Deutschland AG, Leverkusen (DE)

(72) Inventors: Klaus Tidow, Ottenbuttel (DE); Andreas Hecking, Langenfeld (DE); Jan Busch, Dusseldorf (DE); Frank Richter, Leverkusen (DE); Friedhelm Steffens, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/907,591

(22) PCT Filed: Aug. 14, 2014

(86) PCT No.: PCT/EP2014/067432
§ 371 (c)(1),
(2) Date: Jan. 26, 2016

(87) PCT Pub. No.: WO2015/024859
PCT Pub. Date: Feb. 26, 2015

(65) Prior Publication Data
US 2016/0159734 A1   Jun. 9, 2016

(30) Foreign Application Priority Data
Aug. 19, 2013  (EP) ..................................... 13180927

(51) Int. Cl.
*C07C 263/00* (2006.01)
*C07C 263/20* (2006.01)

(52) U.S. Cl.
CPC .................................. *C07C 263/20* (2013.01)

(58) Field of Classification Search
None
See application file for complete search history.

(56) References Cited

U.S. PATENT DOCUMENTS

| | | | |
|---|---|---|---|
| 3,128,310 A | 4/1964 | Koch | |
| 3,331,876 A | 7/1967 | Van Horn et al. | |
| 5,185,384 A * | 2/1993 | Daussin ................ | C07C 263/20 252/182.2 |
| 5,354,432 A | 10/1994 | Arribas et al. | |
| 5,446,196 A | 8/1995 | Benedix et al. | |
| 5,609,735 A | 3/1997 | Hetzel et al. | |
| 7,108,770 B2 | 9/2006 | Grun et al. | |
| 7,118,653 B2 * | 10/2006 | Brady ................... | C07C 263/20 203/100 |
| 7,358,388 B2 | 4/2008 | Wolfert et al. | |
| 7,541,487 B2 | 6/2009 | Pohl et al. | |
| 8,063,241 B2 | 11/2011 | Lorenz et al. | |
| 8,519,190 B2 | 8/2013 | Sasaki et al. | |
| 9,024,057 B2 | 5/2015 | Biskup et al. | |
| 2006/0089507 A1 | 4/2006 | Sohn et al. | |

FOREIGN PATENT DOCUMENTS

| | | | | |
|---|---|---|---|---|
| CA | 1262360 A | * | 10/1989 | .......... C07C 209/86 |
| CA | 2431439 | | 12/2003 | |
| DE | 27 03 313 | | 1/1977 | |
| EP | 1 518 874 | | 8/2004 | |
| GB | 795639 | | 5/1958 | |

OTHER PUBLICATIONS

Twitchett, Chemistry of the production of organic isocyanates, Chem Soc Rev, 1974, 3: 209-230 (abstract).

* cited by examiner

*Primary Examiner* — Sudhakar Katakam
*Assistant Examiner* — Ana Z Muresan
(74) *Attorney, Agent, or Firm* — N. Denise Brown

(57) ABSTRACT

The present invention relates to a process for obtaining organic isocyanate from a phosgenation product comprising the isocyanate, comprising the following steps: a) workup to the phosgenation product, the workup comprising at least one distillation step in which a first portion of the organic isocyanate is removed as distillate and a distillation residue comprising a second portion of the organic isocyanate is obtained, b) workup of the distillation residue obtained in a), the workup comprising at least one distillation step which is conducted at a temperature of up to 110° C. at a pressure of not more than 1 mbar, wherein at least 50% by weight of the second portion of the organic isocyanate is removed from the distillation residue.

15 Claims, 1 Drawing Sheet

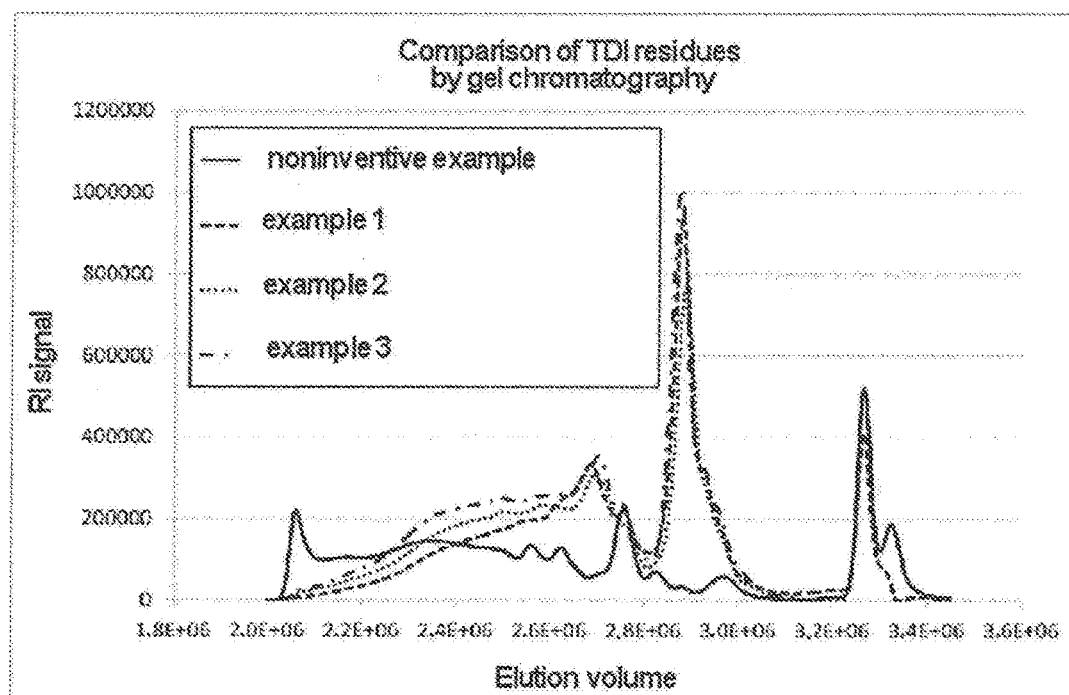

PROCESS FOR OBTAINING ORGANIC ISOCYANATES FROM DISTILLATION RESIDUES FROM ISOCYANATE PREPARATION

CROSS-REFERENCE TO RELATED APPLICATIONS

This Application is a National Phase Application of PCT/EP2014/067432, filed Aug. 14, 2014, which claims priority to European Application No. 13180927.9, filed Aug. 19, 2013, each of which being incorporated herein by reference.

FIELD

The present invention relates to a process for obtaining an organic isocyanate from a phosgenation product comprising the isocyanate.

BACKGROUND

The production of di-or polyisocyanates such as tolylene diisocyanate (TDI) by phosgenation of tolylene diamine (TDA) and the subsequent distillative purification of the crude isocyanate, i.e. of the TDI, are common knowledge. Common to all of the known processes for distillative purification of the crude TDI is that the distillation affords not only the desired purified TDI but also higher-boiling components which, as a minimum, need to be made suitable for sending for proper disposal. The prior art for treatment of so-called distillation residues from TDI production describes various processes. General aims for residue treatment are maximization of the TDI yield, minimization of the amount of residue generated and a very useful, cost-effective and simple recycling of the residue amount no longer usable in the TDI production process. The workup of residues from isocyanate production is of increasing economic interest since the amount of residue and the amount of material of value present therein increases with increasing plant size.

The thermally induced undesired formation of higher polymers from diisocyanates by reaction with traces of moisture, amines and with one another to form, for example, ureas, uretdiones, biurets, isocyanurates, carbodiimides and uretonimines is common knowledge and often described in the literature. Substantial disadvantages of these undesired side reactions are that the formation thereof consumes material of value (TDI) and that they result in uncontrollable polymer growth which is accompanied by an increase in viscosity. This is the case in particular for residue concentrations in excess of >10% in TDI. In many cases the polymer growth likewise results in compounds that are insoluble in organic solvents. Such residues are thus convertible into solutions easily handleable in terms of process engineering only at comparatively greater effort and in low concentrations. Only a small number of costly and inconvenient processes have been brought to bear for such residues due to the poor handleability thereof. The economic efficiency of the workup of such residues is thus further significantly reduced.

To minimize the isocyanate yield losses the distillation residue may be transferred into a stirred and heated container and mixed with high-boiling hydrocarbons, preferably bitumen, inert under the distillation conditions to distill-off the free isocyanate still present in the residue as completely as possible (EP 0 548 685 A2). The remaining residue freed of isocyanate may be discharged as a free-flowing solid and sent for incineration. Disadvantages of this process include not only the use of a substance foreign to the process (bitumen) but also yield losses due to polymerization of the isocyanate since the process includes high residence times at high temperature.

A further process for isocyanate residue removal comprises using kneader dryers (EP 0 626 368 A1). In this process the abovedescribed heated and stirred containers are replaced by kneader dryers The use of, for example, bitumen has the effect that as in the abovementioned example the remaining residue is obtained as a free-flowing solid which may be employed as a fuel in cement works for example. An advantage of this process compared to the abovementioned process is an increase in yield while the required higher capital expenditure resulting from the more complex technology may be seen as a disadvantage. The use of mechanically moving parts also inevitably results in higher maintenance costs.

EP 0 699 659 A2 describes a process and an apparatus for removing a solid residue from a solution of the residue in vaporizable materials of value and/or solvents by adding up to 20 wt % of high-boiling hydrocarbons inert toward the materials of value under the evaporation conditions and heating the mixture to the evaporation temperature under vacuum, wherein the materials of value evaporate and are drawn off and condensed and the residue is obtained as a free-flowing solid, wherein the residue solution is applied to a stirred bed of granular, solid material which is kept at evaporation temperature. The disadvantage of this process is the additional use of high-boiling solvents which need to be worked up in a further process.

Hydrolysis of isocyanate distillation residues with water to achieve recovery of the starting amine, in particular in the production of TDI, is a field that has been worked on for a comparatively long time already and is described in U.S. Pat. No. 3,128,310, U.S. Pat. No. 3,331,876, GB 795,639, DE 27 03 313 A1 and EP 1 935 877 A1 for example. The cited processes comprise hydrolyzing isocyanate distillation residue with water at elevated pressure and elevated temperature. This converts a portion of the residue into the starting amine which after appropriate workup may be fed back into the phosgenation process thus resulting in residue minimization. What is unsatisfactory in these processes is that a portion of the isocyanate product of value needs to be hydrolyzed back to the starting material and phosgenated again. While this does send the isocyanate present in the residue for useful material recycling it would be desirable to be able to recover from the residue the isocyanate as such.

WO 2007/007887 of Mitsui Chemicals Polyurethanes, Inc. discloses an isocyanate crude product workup which describes not only distillative isocyanate purification but also a two-stage residue concentration. The residue-containing mixture may then optionally be subjected to a hydrolysis reaction which permits recovery of the starting amine. This comprises sending the isocyanate crude product freed of solvent to a distillation column, isocyanate being distilled off under reduced pressure and elevated temperature and residue-containing bottoms product being discharged. This bottoms product has a preferred residue content of 10-40 wt % based on the isocyanate/residue mixture and is conveyed into the second stage of the residue concentration using a pump. This second stage is composed, for example, of a thin-film evaporator which is operated at reduced pressure and comprises an internal condenser. In this evaporator isocyanate is removed, condensed and discharged, an isocyanate-containing residue fraction being transferred to a further processing operation, for example a residue hydrolysis, via a pump. The second concentration stage enriches the residue content to preferably 45-80 wt %, the chlorine content of this fraction being preferably not more than 1.5 wt %, corresponding to 15 000 ppm. Cited as advantages of the described process are the removal of volatile chlorine compounds even in the first concentration stage and the short residence time in the second stage which aims to suppress the continuing viscosity increase through thermally induced polymerization. A disadvantage of such a procedure is that the reported chlorine contents of >1 wt % absolutely still promote thermally induced polymerization in the second stage (which is not operated in pressure- and temperature-optimized fashion) thus leading to not insignificant thermal residue formation which is accompanied by a loss of material of value (TDI). The further workup by residue hydrolysis which follows the residue concentration appears uneconomical and inconvenient for the reported concentrations since while only the still present residual content of material of value (TDI) may be converted back into starting amine by hydrolysis the entire obtaining residue needs to be subjected to the hydrolysis which in turn necessitates a corresponding workup.

DE 102 60 092 relates to a process for purifying crude isocyanate streams in which residue-containing streams are removed in two different steps. To this end the crude isocyanate stream is initially resolved into a residue-containing stream and a gaseous stream in evaporation. While the residue-containing stream is further freed of isocyanate product in a kneader dryer or paddle dryer the gaseous stream is subjected to distillative separation to afford three substreams consisting essentially of low-boiler components, isocyanate product and a further residue-containing stream. The vapor stream from the dryer stage consisting largely of isocyanate product is sent to said distillative separation together with the gaseous stream from the first evaporation optionally after condensation. One disadvantage of this process is that it requires that residue streams be withdrawn and sent for recycling at two different points of the workup.

DE 102 60 093 describes a process for removing isocyanates from a reaction mixture, wherein the reaction mixture freed of the solvent is separated into three fractions in a single separation stage. This affords a tops product composed predominantly of hydrogen chloride and phosgene which is sent for destruction. At the side draw of the column TDI still comprising chlorinated byproducts is withdrawn. TDI and TDI-containing high boilers accumulate at the bottom of the column. In a downstream evaporation crude TDI is again obtained from this high boiler fraction and sent to the TDI obtaining from the side draw. The tar-like residue obtained in the bottoms is likewise sent for incineration. However this document neither describes the residue concentrations achieved in the evaporative concentration nor mentions a concentration of detectable NCO content in the tar-like residue. It further fails to mention that the obtained crude TDI (from bottoms and side draw) is subjected to further purification steps which is absolutely necessary due to the very high content of chlorinated byproducts and which again has a negative influence on the yield balance. It is thus moot whether the described process is a process having economic/large-industrial-scale practicability.

EP 1 413 571 A1 and EP 1 371 633 A1 are concerned with optimizing the workup of TDI by employing a dividing wall column in the distillation which results, inter alia, in a reduction in the content of TDI in the bottoms product. However, accumulation of an isocyanate-containing distillation residue cannot be prevented here either.

SUMMARY

The present invention has for its object the provision of an improved process for processing phosgenation products, in particular for obtaining an organic isocyanate from a phosgenation product comprising the isocyanate. This process shall remove a very high fraction of the organic isocyanates formed in the phosgenation. The loss of organic isocyanates degraded by undesired chemical reactions and the residue amount shall on the whole be kept very low and the remaining residue shall be very easily removable after processing.

Surprisingly, the object was solved by sending the mixture comprising TDI and higher-boiling components to by means of a mild, rapid, two-stage continuous distillation. The present invention thus provides a process for obtaining an organic isocyanate from a phosgenation product comprising the isocyanate, comprising the steps of:
a) working up the phosgenation product, wherein the workup comprises at least one distillation step where a first portion of the organic isocyanate is removed as distillate and a distillation residue comprising a second portion of the organic isocyanate is obtained,
b) working up the distillation residue obtained in a), wherein the workup comprises at least one distillation step carried out at a temperature of up to 110° C. at a pressure of not more than 1 mbar, wherein at least 50 wt % of the second portion of the organic isocyanate is removed from the distillation residue.

BRIEF DESCRIPTION OF THE DRAWING

The FIGURE is a graph illustrating mathematical evaluation of the results of GPC analysis b) polydispersity of the concentrates of the Examples.

DETAILED DESCRIPTION

In an advantageous implementation of the process according to the invention the distillation step of the workup b) is carried out at a temperature of up to 90° C. and/or at a pressure of not more than 1 mbar, in particular at not more than 0.8 mbar, preferably at not more than 0.5 mbar, particularly preferably at not more than 0.3 mbar, very particularly preferably at not more than 0.1 mbar. In this way even milder conditions for the processing of the organic isocyanates may be employed to further reduce the risk of the isocyanates undergoing undesired reactions. All pressures reported in the context of the present invention are absolute pressures.

In the context of the present invention it is further preferred when the residence time of the distillation residue in the distillation step of the workup b) is not longer than 30 minutes, preferably not longer than 15 minutes. The short residence period allows the amount of organic isocyanates degraded by undesired reactions to be kept low.

Furthermore, the distillation step of the workup b) can remove at least 60 wt % of the second portion of the organic isocyanate from the distillation residue, in particular at least 70 wt %.

For polymers it is typical to report average molar mass values Mn and Mw and the width of the distribution D. The established measure for the width of a distribution is the polydispersity D. The polydispersity value is of importance since both distributions may have the same weight-average molar mass Mw while nevertheless having distinct distributions (and thus distinct macroscopic properties). Polydispersity is defined as the quotient of Mw and Mn (D=Mw/Mn) and represents an independent reckoning basis for determining the molecular weight distribution of a polymeric compound. As a parameter for the thermally induced polymerization occurring during concentration the change in the relatively high molecular weight fraction before and after TDI removal may be described by $\Delta D$. During the workup b) thermally induced polymerization of the organic isocyanate is preferably very substantially prevented so that for the change in the polydispersity $\Delta D$ of the relatively high molecular weight fraction having a weight-average molar mass of more than 500 g/mol before and after the workup b) $\Delta D<3.0$, in particular $\Delta D<2.0$. This may be achieved, for example, by the abovementioned short residence times, the cited temperatures and/or pressures.

The phosgenation products employed in the context of the process according to the invention may have been prepared in any way known to those skilled in the art. The phosgenation product is, for example, obtained by phosgenation of a primary organic amine, wherein the phosgenation product comprises the corresponding organic isocyanate. This phosgenation is, in particular, carried out in the gas phase. This comprises reacting the organic amine, in particular an aromatic amine, with phosgene in the gas phase preferably according to the teaching of EP 1 935 876 (adiabatic reaction procedure), particularly preferably as per EP 2 196 455, at a temperature above the boiling point of the amines in a reactor comprising a reaction space which is substantially rotationally symmetric in the flow direction to afford the phosgenation product crude isocyanate.

Primary organic amines that may be employed include aromatic di-, tri- or polyamines, in particular toluenediamine Suitable organic isocyanates include in particular aromatic di-, tri- or polyisocyanates, in particular tolylene diisocyanate. However it is likewise possible to employ aliphatic and cyclic amines/isocyanates in the process according to the invention. The tolylene diisocyanate preferably comprises at least 80 wt %, in particular at least 90 wt %, of the 2,4-tolylene diisocyanate isomer.

The content of hydrolyzable chlorine (HC) essentially indicates the amount of hydrogen chloride still bonded to the isocyanate in the form of carbamoyl chloride. The HC content further captures compounds formed during the phosgenation as byproducts from the reaction of phosgene and the previously formed isocyanate by cleavage of CO2 formed carbodiimides as also postulated by H. J. Twichett in Chem. Soc. Rev., 1974,3, 209-230. It is known that compounds comprising hydrolyzable chlorine decompose into hydrogen chloride and isocyanate under the action of heat. It is further known that compounds comprising hydrolyzable chlorine promote thermally induced polymerization and the presence of compounds comprising hydrolyzable chlorine is therefore a substantial disadvantage. Typical distillation bottoms of comparable concentrations have a content of hydrolyzable chlorine in the region of 10 000 ppm. A reliable method of determining the content for hydrolyzable chlorine is potentiometric titration where the sample for determining the HC content is urethanized using methanol and subsequently hydrolyzed using water. The thus formed ionogenic chlorine is acidified with nitric acid and then subjected to argentometric titration against a silver nitrate solution. According to a further embodiment of the process according to the invention the distillation residue obtained after the workup a) exhibits a content of hydrolyzable chlorine compounds of less than 2000 ppm, in particular less than 1500 ppm, without any further workup.

In the process according to the invention the distillation residue obtained after step b) preferably has an NCO content of at least 20 wt %, in particular at least 25 wt %. The NCO content is determined by titration as per DIN EN ISO 11 909. The residue concentration is determined in by means of a mass balance expressed as a percentage, to this end the amount of residue concentrate to be determined is freed of vaporizable fractions for 30 minutes at 220° C. and a pressure of less than 1 mbar, the calculation being performed as per:

$$\% \text{ residue concentration} = \frac{(\text{g residue (final weight)})}{(\text{g residue determination initial weight} * 100)}$$

The loss of detectable NCO groups serves as a measure for the thermally induced polymerization occurring during the concentration which may be accelerated by the presence of chlorine-containing secondary components. When the decrease in the NCO content surpasses that of the increase in residue (residue concentration increase) the described undesired polymerization takes place. The residual content of organic isocyanate in the distillation residue obtained after step b) may be, for example, up to 30 wt %, in particular up to 25 wt %, preferably up to 20 wt %, for example from 20 to 30 wt %.

In the process according to the invention the distillation residue obtained after step b) may have a solubility in aprotic polar solvents having an elution power of greater than 0.55 e° with Al2O3 as the adsorbent of up to 90 wt % at room temperature for example. The elution power e° is the relative adsorption energy for each solvent on aluminium oxide.

Suitable aprotic polar solvents include in particular ethyl acetate or acetone. This is particularly advantageous since on this allows for easier removal of the distillation residues than for the processes known to date. This is made possible in particular by the mild processing conditions at reduced temperature/pressure upon which the process according to the invention is based. Thus a preferred implementation of the process according to the invention is characterized in that the distillation residue obtained after step b) is at least partially dissolved and removed from the distillation plant in an aprotic polar solvent having an elution power greater than 0.55 e° with $Al_2O_3$ as the adsorbent, in particular in ethyl acetate or acetone. As specified hereinabove, for example, up to 90 wt % of the distillation residue may be dissolved at room temperature. This affords low-viscosity solutions that are easily handleable in terms of process engineering and that may be pumped away and, for example, stored at room temperature.

The distillation steps performed in the context of the process according to the invention may in principle be carried out in any way known to those skilled in the art. The distillation step of the workup a) and/or the workup b) is preferably carried out using a forced discharge evaporator, in particular using a single-pass evaporator, falling-film evaporator, long-tube evaporator, falling-tube evaporator, thin-film evaporator or short-path evaporator, particularly preferably using a thin-film evaporator or short-path evaporator.

EXAMPLES

The invention will now be more particularly discussed with reference to examples. In the examples all percentage values relate to weight. The determination of the NCO content of the concentrates described in the examples and comparative examples was performed by titration according to DIN EN ISO 11 909. The purity and isomer ratio of the TDI were determined by gas chromatography. The measurements were performed using an HP 5890 from Hewlett Packard with an FID detector and HP-Chemstation software using an HP 35 column, 2,4-TDI from Merck having article no. 808264 serving as reference.

The liquid product stream, the crude isocyanate, is subsequently sent to a distillative, generally multistage workup and dissolved phosgene and the solvent are removed. This distillative workup of the crude isocyanate may be performed according to common knowledge methods. Examples are described at length in EP-371 635 B1 and EP 1 413 571 B1.

EP 1 371 635 B1 paragraph [0053] concerns a two-stage workup comprising initially removing a substantial part of the solvent and all of the low-boiling components, for example dissolved phosgene, from the crude isocyanate in a first distillation column The solvent removed at the top of the column, optionally freed of the low-boiling components in further purification steps, is returned to the phosgenation process.

A mixture composed of the remaining solvent, the product TDI and the higher-boiling components is obtained in the bottoms from the column. In a second distillation column the remaining solvent is then removed at the top of the column. The pure TDI may be withdrawn as distillate in the sidestream of the distillation configured as a dividing wall column A mixture of relatively high-boiling components and TDI is obtained in the bottoms from the dividing wall column. According to the example EP 1 371 635 B1 the concentration of relatively high-boiling components is from 0.5 to 15 wt %.

The distillative workup of the mixture produced by the process according to the invention and composed of TDI and higher-boiling components is preferably performed according to one of the three examples shown hereinbelow.

Example 1

A mixture comprising 90% TDI and 10% higher-boiling components is sent to a vacuum distillation in a thin-film evaporator (V2) with an upstream preevaporator (V1) at a feed rate of 840 ml/h. The first evaporator stage (V1) resolves the mixture into 30% bottoms effluent (S1) and 70% distillate (D1) at 85° C. (T(V1)) and 0.5 mbar (p(V1)). The distillate (D1) thus obtained comprises 99.7% TDI w(TDI; D1) with a fraction of 2,4-isomer of 88.6%. The bottoms effluent (S1) is sent immediately to the second evaporator stage (V2). V2 in turn separates said effluent into a bottoms effluent S2 and distillate D2 at 140° C. (T(V2)) and 0.5 mbar (p(V2)). The distillate D2 thus obtained comprises 99.3% TDI w(TDI; D2) with a fraction of 2,4-isomer of 90.2%. The concentrate obtained, bottoms effluent S2, has a residue concentration w(S2)=69.9% and an NCO content w(NCO; S2)=29.4%.

Example 2

Similarly to example 1 the mixture comprising 90% TDI and 10% higher-boiling components is sent to a vacuum distillation in a thin-film evaporator (V2) with an upstream preevaporator (V1) at a feed rate of 780 ml/h. The first evaporator stage (V1) resolves the mixture into 25% bottoms effluent (S1) and 75% distillate (D1) at 80° C. (T(V1)) and 0.4 mbar (p(V1)). The distillate (D1) thus obtained comprises 99.6% TDI w(TDI; D1) with a fraction of 2,4-isomer of 88.3%. The bottoms effluent (S1) is sent immediately to the second evaporator stage (V2). V2 in turn separates said effluent into a bottoms effluent S2 and distillate D2 at 145° C. (T(V2)) and 0.4 mbar (p(V2)). The distillate D2 thus obtained comprises 99.4% TDI w(TDI; D2) with a fraction of 2,4-isomer of 90.6%. The concentrate obtained, bottoms effluent S2, has a residue concentration w(S2)=78.7% and an NCO content w(NCO; S2)=27.5%.

Example 3

Similarly to example 1 the mixture comprising 90% TDI and 10% higher-boiling components is sent to a vacuum distillation in a thin-film evaporator (V2) with an upstream preevaporator (V1) at a feed rate of 780 ml/h. The first evaporator stage (V1) resolves the mixture into 20% bottoms effluent (S1) and 80% distillate (D1) at 80° C. (T(V1)) and 0.3 mbar (p(V1)). The distillate (D1) thus obtained comprises 99.7% TDI w(TDI; D1) with a fraction of 2,4-isomer of 88.1%. The bottoms effluent (S1) is sent immediately to the second evaporator stage (V2). V2 in turn separates said effluent into a bottoms effluent S2 and distillate D2 at 130° C. (T(V2)) and 0.3 mbar (p(V2)). The distillate D2 thus obtained comprises 99.2% TDI w(TDI; D2) with a fraction of 2,4-isomer of 91.0%. The concentrate obtained, bottoms effluent S2, has a residue concentration w(S2)=62.9% and an NCO content w(NCO; S2)=30.0%.

Comparative Example

A mixture comprising 13% ODB, 67% TDI and 20% higher-boiling components is sent to a stirred tank at a feed rate of about 2300 L/h. The tank is operated under reduced pressure (ca. 20-30 mbar) and the tank-bottom temperature is about 140 to 150° C. The mixture is resolved into distillate and bottoms effluent under these conditions. The concentrate obtained has a residue concentration of 55% and an NCO content w(NCO)=18.5%.

The concentrates from examples 1 to 3 and from the comparative example were analyzed in respect of their polydispersity by GPC. The determination range for the column set employed was in the range between 100 and 20 000 Da. Evaluation was carried out using WIN GPC from Polymer Standard Services GmbH, Mainz. The mathematical evaluation of the results is summarized in Table 1 and the graphical evaluation is shown in the FIGURE.

As previously described by way of introduction the parameter D has become established as an independent value for describing polydispersity and provides information about molecular weight distribution. By this measure the samples prepared in accordance with the invention show a markedly lower polydispersity than the comparative example.

TABLE 1 results of GPC evaluation

| | TDI residue | | | |
|---|---|---|---|---|
| | Mn | Mw | Mz | D |
| comparative example (noninventive) (55 wt %) | 325 | 1480 | 4061 | 4.6 |
| example 1 (inventive) (71 wt %) | 344 | 619 | 1346 | 1.8 |
| example 2 (inventive) (81 wt %) | 488 | 810 | 1687 | 1.7 |
| example 3 (inventive) (62 wt %) | 499 | 736 | 1337 | 1.5 |

The invention claimed is:

1. A process for obtaining an organic isocyanate from a phosgenation product comprising the isocyanate, comprising:
   a) working up the phosgenation product, wherein the workup comprises at least one distillation step where a first portion of the organic isocyanate is removed as distillate and a distillation residue comprising a second portion of the organic isocyanate is obtained, and
   b) working up the distillation residue obtained in a), wherein the workup comprises at least one distillation step carried out at a temperature of up to 110° C. at a pressure of not more than 1 mbar, wherein at least 50 wt % of the second portion of the organic isocyanate is removed from the distillation residue.

2. The process of claim 1, wherein the distillation step of the workup b) is carried out at a temperature of up to 90° C. and/or at a pressure of not more than 1 mbar.

3. The process of claim 1, wherein the residence time of the distillation residue in the distillation step of the workup b) is not longer than 30 minutes.

4. The process of claim 1, wherein the distillation step of the workup b) removes at least 60 wt % of the second portion of the organic isocyanate from the distillation residue.

5. The process of claim 1, wherein during the workup b) thermally induced polymerization of the organic isocyanate is very substantially prevented so that for the change in the polydispersity ΔD of the relatively high molecular weight fraction having a weight-average molar mass of more than 500 g/mol before and after the workup b) ΔD<3.0.

6. The process of claim 1, wherein the phosgenation product is obtained by phosgenation of a primary organic amine, wherein the phosgenation product comprises the corresponding organic isocyanate and wherein the phosgenation is carried out in the gas phase.

7. The process of claim 6, wherein the primary organic amine is an aromatic di-, tri- or polyamine, and the organic isocyanate is an aromatic di-, tri- or polyisocyanate.

8. The process of claim 7, wherein the aromatic di-, tri- or polyisocyanate comprises tolylene diisocyanate comprising at least 80 wt % of the 2,4-tolylene diisocyanate isomer.

9. The process of claim 1, wherein the distillation residue obtained after the workup a) exhibits a content of hydrolyzable chlorine compounds of less than 2000 ppm without any further workup.

10. The process of claim 1, wherein the distillation residue obtained, after step b) has an NCO content of at least 20 wt %.

11. The process of claim 1, wherein the residual content of organic isocyanate in the distillation residue obtained after step b) is up to 30 wt %.

12. The process of claim 1, wherein the distillation residue obtained after step b) is at least partially dissolved and removed from the distillation plant in an aprotic polar solvent having an elution power greater than 0.55 e° with $Al_2O_3$ as the adsorbent.

13. The process of claim 1, wherein the distillation step in the workup a) and/or the workup b) is carried out using as forced discharge evaporator.

14. The process of claim 12 wherein the aprotic polar solvent comprises ethyl acetate or acetone.

15. The process of claim 13 wherein the forced discharge evaporator comprises a single-pass evaporator, a falling film evaporator, a long tube evaporator, a falling tube evaporator, a thin-film evaporator or a short-path evaporator.

* * * * *